(12) United States Patent
Takahashi et al.

(10) Patent No.: US 8,785,671 B2
(45) Date of Patent: Jul. 22, 2014

(54) 6,13-DIHALOGEN-5,14-DIHYDROPENTACENE DERIVATIVE AND METHOD FOR PRODUCING 6,13-SUBSTITUTED-5,14-DIHYDROPENTACENE DERIVATIVE USING SAME

(75) Inventors: Tamotsu Takahashi, Sapporo (JP); Ken-ichiro Kanno, Sapporo (JP); Shi Li, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 134 days.

(21) Appl. No.: 13/261,420

(22) PCT Filed: Mar. 4, 2011

(86) PCT No.: PCT/JP2011/055089
§ 371 (c)(1),
(2), (4) Date: Nov. 27, 2012

(87) PCT Pub. No.: WO2011/108712
PCT Pub. Date: Sep. 9, 2011

(65) Prior Publication Data
US 2013/0079530 A1   Mar. 28, 2013

(30) Foreign Application Priority Data
Mar. 4, 2010   (JP) .................. 2010-047726

(51) Int. Cl.
*C07F 19/00*   (2006.01)
*C07C 13/62*   (2006.01)

(52) U.S. Cl.
CPC ...................................... *C07C 13/62* (2013.01)
USPC ......................................................... 556/22

(58) Field of Classification Search
CPC .................................................... C07C 13/62
USPC ......................................................... 556/22
See application file for complete search history.

(56) References Cited

U.S. PATENT DOCUMENTS

2003/0116755 A1   6/2003   Takahashi

FOREIGN PATENT DOCUMENTS

JP   2006-248923 A   9/2006
JP   2008-163031 A   7/2008

OTHER PUBLICATIONS

Allen et al., "Action of Grignard Reagents on Certain Pentacene quinones, 6,13-Diphenylpentacene," J. Am. Chem. Soc., 1941, 64:1253-1260.
Jia et al., "Preparation of 6,13-Bis(trimethylsilyl)pentacene and Formation of Second-Ring Diels-Alder Adduct of Pentacene," J. Org. Chem., 2011, 76:293-296.
Kaur et al., "Substituent Effects in Pentacenes: Gaining Control over HOMO-LUMO Gaps and Photooxidative Resistances," J. Am. Chem. Soc., 2008, 130:16274-16286.
Maulding et al., "Electronic Absorption and Fluorescence of Phenylethynyl-Substituted Acenes," J. Org. Chem., 1969, 34:1734-1736.
Takahashi et al., "Isolation of 6,13-Dipropylpentacene and Its Tautomerization," J. Am. Chem. Soc., 2007, 129:15752-15753.
Vets et al., "Reduction versus Rearrangement of 6,13-Dihydro-6,13-diarylpentacene-6,13-Diols Affording 6,13- and 13,13'-Substituted Pentacene Derivatives," Synlett, 2005, 2:217-222.

*Primary Examiner* — Taofiq A Solola
(74) *Attorney, Agent, or Firm* — Foley & Lardner LLP

(57) ABSTRACT

The present invention provides a 6,13-dihalogen-5,14-dihydropentacene derivative and a method for production thereof. Compounds (b) and (c) are reacted through cross-coupling reaction in the presence of a metal compound and a lithiating agent to synthesize compound (d), which is then halogenated to thereby obtain a 6,13-dihalogen-5,14-dihydropentacene derivative (compound (e)).

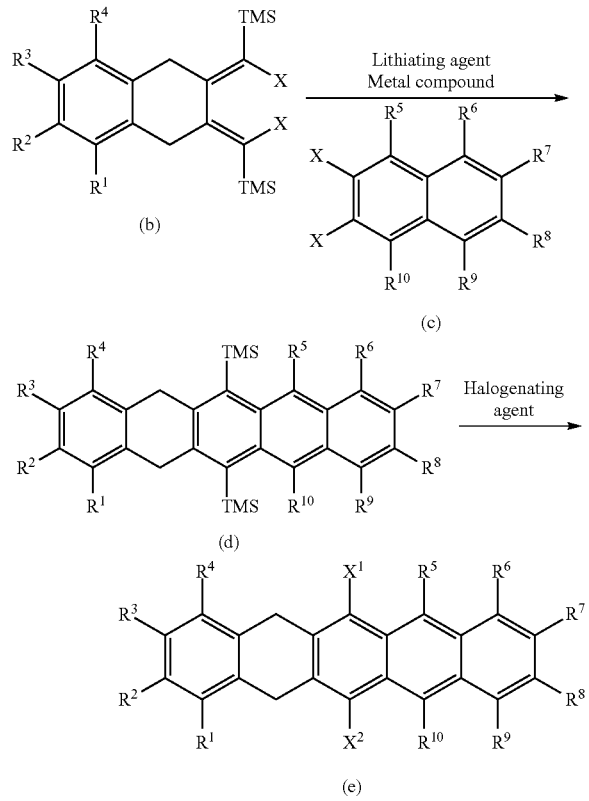

[wherein $X^1$ and $X^2$ are each a halogen atom, and $R^1$, $R^2$, $R^3$, $R^4$, $R^5$, $R^6$, $R^7$, $R^8$, $R^9$ and $R^{10}$ are each a hydrogen atom, an optionally substituted $C_1$-$C_{20}$ hydrocarbon group, etc.]

14 Claims, 1 Drawing Sheet

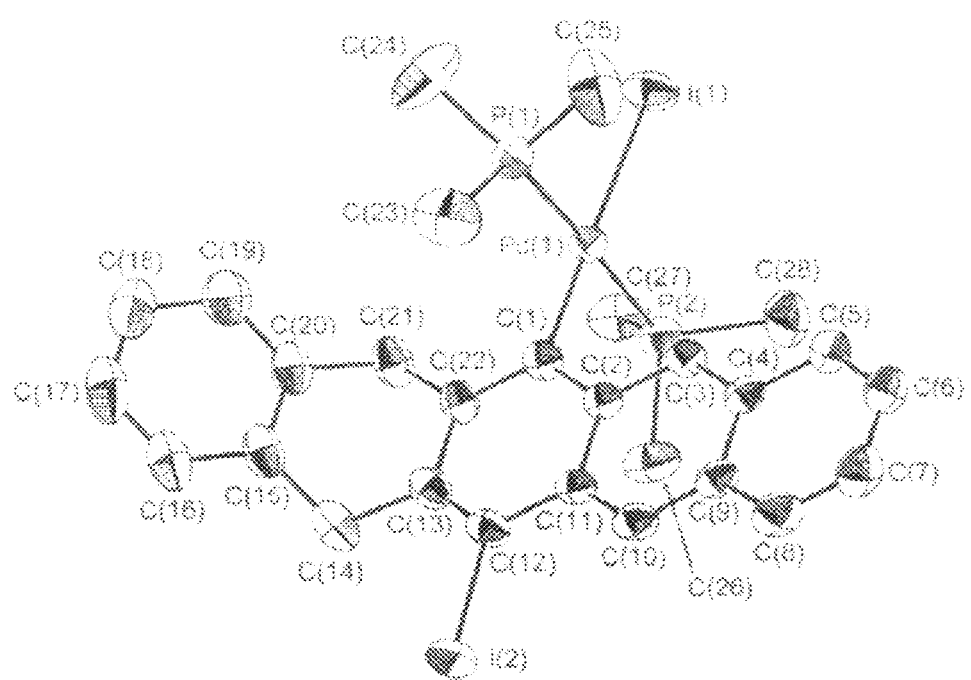

6,13-DIHALOGEN-5,14-DIHYDROPENTACENE DERIVATIVE AND METHOD FOR PRODUCING 6,13-SUBSTITUTED-5,14-DIHYDROPENTACENE DERIVATIVE USING SAME

CROSS-REFERENCE TO RELATED APPLICATIONS

This application is a National Stage application of PCT/JP2011/055089, filed Mar. 4, 2011, which claims priority from Japanese application JP 2010-047726, filed Mar. 4, 2010.

TECHNICAL FIELD

The present invention relates to a 6,13-dihalogen-5,14-dihydropentacene derivative and a method for producing a 6,13-substituted 5,14-dihydropentacene derivative using the same. The present invention also relates to a method for producing a 6,13-substituted pentacene derivative.

BACKGROUND ART

Polyacene compounds including pentacene have now received attention as organic electronic materials for organic semiconductors or organic electroconductive materials, etc. However, it is not easy to introduce a substituent of any type at any position of the side chain on the polyacene skeleton, and hence there has been a demand for achieving simpler production of a desired compound.

For introduction of substituents at the 6- and 13-positions of the pentacene skeleton, the method of Maulding et al. has been known (Non-patent Document 1: D. R. Maulding, and Bernard G Roberts "Electronic absorption and fluorescence of phenylethynyl-substituted acenes" J. Org. Chem., 34, 1969, pp 1734). In the method of Maulding et al., pentacenequinone is reacted with Grignard reagents to thereby introduce substituted alkynylene groups at the 6- and 13-positions of the pentacene skeleton (see the scheme shown below).

[Formula 1]

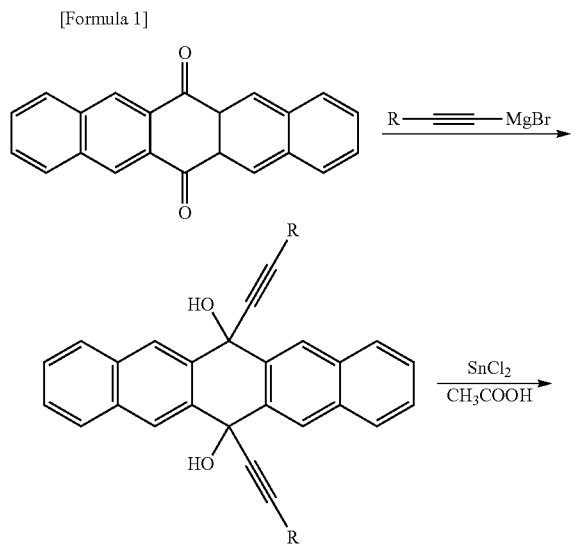

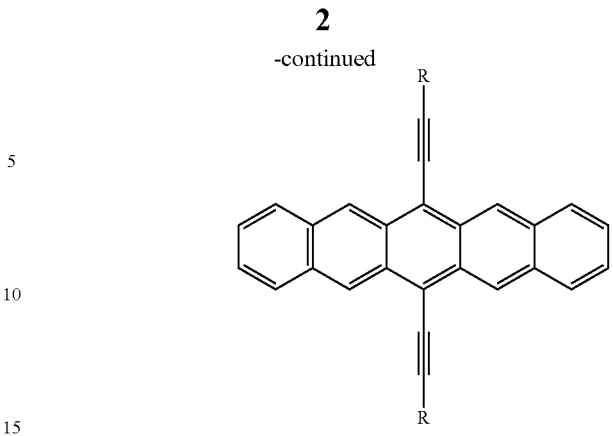

Moreover, for synthesis of a pentacene derivative using pentacenequinone as a starting compound, the method of Miller et al. has also been known (Non-patent Document 2: Kaur, W. Jia, R. P. Kopreski, S. Selvarasah, M. R. Dokmeci, C. Pramanik, N. E. McGruer, G P. Miller "Substituent Effects in Pentacenes: Gaining Control over HOMO-LUMO Gaps and Photooxidative Resistances" J. Am. Chem. Soc., 130, 2008, pp 16274). In the method of Miller et al., pentacenequinone is reduced to convert its 6- and 13-positions into hydroxy groups, which are then replaced with alkylthiol groups, finally followed by aromatization with chloranil to thereby introduce alkylthio groups (see the scheme shown below).

[Formula 2]

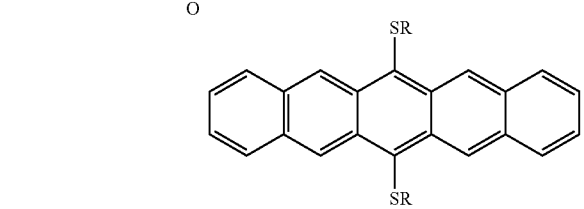

However, these conventional methods have problems in that desired compounds cannot be obtained in high yields or are difficult to isolate because side reactions may occur in these methods.

For example, during reaction between pentacenequinone and thienyl groups, there is a risk that substituents on the thienyl groups will cause a reaction by which two thienyl groups are transferred to the same side during diol formation (Non-patent Document 3: N. Vets, M. Smet, W. Dehaen, "Reduction versus Rearrangement of 6,13-Dihydro-6,13-diarylpentacene-6,13-diols Affording 6,13- and 13,13-Substituted Pentacene Derivatives, Substituted Nephtacaenes and Pentacenes" SYNLETT 2005, pp 0217).

Moreover, during reaction between pentacenequinone and phenyl Grignard, 1,4-addition reaction will occur that does not target the carbonyls at the 6- and 13-positions of pentacene, but attacks their adjacent rings, so that a phenyl group is attached to the second ring (Non-patent Document 4: C. F. H. Allen, A. Bell "Action of Grignard Reagents on Certain Pentacenequinones, 6,13-Diphenylpentacene" J. Am. Chem. Soc., 64, 1942 pp 1253).

Furthermore, it is well known that upon reaction with alkyllithium or alkyl Grignard reagents in an attempt to introduce alkyl groups at the 6- and 13-positions of pentacene, isomerization reaction will occur and desired compounds cannot be obtained at all. In this conventional method starting with pentacenequinone, nobody has succeeded in introducing alkyl groups.

In contrast, the inventors of the present invention have proposed a new approach to form the pentacene skeleton, which involves synthesis of a starting material having alkyl substituents and the subsequent coupling reaction with a diiodo compound. The inventors of the present invention have suggested that the above problems associated with alkyl groups can be avoided, and have reported that alkyl groups can actually be introduced at the 6- and 13-positions of pentacene (Non-patent Document 5: T. Takahashi, K. Kashima, S. Li, K. Nakajima, K. Kanno "Isolation of 6,13-Dipropylpentacene and its tautomerization" J. Am. Chem. Soc., 129, 2007, pp 15752).

PRIOR ART DOCUMENTS

Non-Patent Documents

Non-patent Document 1: D. R. Maulding, and Bernard G Roberts "Electronic absorption and fluorescence of phenylethynyl-substituted acenes" J. Org. Chem., 34, 1969, pp 1734

Non-patent Document 2: Kaur, W. Jia, R. P. Kopreski, S. Selvarasah, M. R. Dokmeci, C. Pramanik, N. E. McGruer, G P. Miller "Substituent Effects in Pentacenes: Gaining Control over HOMO-LUMO Gaps and Photooxidative Resistances" J. Am. Chem. Soc., 130, 2008, pp 16274

Non-patent Document 3: N. Vets, M. Smet, W. Dehaen, "Reduction versus Rearrangement of 6,13-Dihydro-6,13-diarylpentacene-6,13-diols Affording 6,13- and 13,13-Substituted Pentacene Derivatives, Substituted Nephtacaenes and Pentacenes" SYNLETT 2005, pp 0217

Non-patent Document 4: C. F. H. Allen, A. Bell "Action of Grignard Reagents on Certain Pentacenequinones, 6,13-Diphenylpentacene" J. Am. Chem. Soc., 64, 1942 pp 1253

Non-patent Document 5: T. Takahashi, K. Kashima, S. Li, K. Nakajima, K. Kanno "Isolation of 6,13-Dipropylpentacene and its tautomerization" J. Am. Chem. Soc., 129, 2007, pp 15752

SUMMARY OF THE INVENTION

Problem to be Solved by the Invention

As described above, there has been a demand for a method for producing a pentacene derivative having substituents at the 6- and 13-positions of the pentacene skeleton in a simpler manner with high selectivity.

Means to Solve the Problem

As described above, the inventors of the present invention have already reported that coupling reaction with a diiodo compound allows the solution of problems in prior art techniques and enables the introduction of alkyl groups at the 6- and 13-positions of pentacene. However, in this method, substituents are introduced into a starting material before the pentacene skeleton is formed. If substituents of any type can be introduced after the pentacene skeleton is formed, such an approach will be simpler as a production method and will have a wider range of applications.

As a result of extensive and intensive efforts made to solve the problems stated above, the inventors of the present invention have first found that substituents of various types can be introduced with high selectivity at the 6- and 13-positions of a 5,14-dihydropentacene compound when a 6,13-dihalogenated dihydropentacene derivative whose 6- and 13-positions are substituted with halogen atoms is synthesized and reacted with various organometallic compounds through cross-coupling reaction. The inventors of the present invention have further found that a pentacene derivative having substituents of any type at the 6- and 13-positions can be produced with high selectivity upon aromatization of the resulting 6,13-substituted 5,14-dihydropentacene derivative. These findings led to the completion of the present invention.

Namely, as shown below, the present invention relates to a 6,13-dihalogen-5,14-dihydropentacene derivative and a method for producing a 6,13-substituted 5,14-dihydropentacene derivative using the same, as well as a method for producing a 6,13-substituted pentacene derivative, etc.

[1] A 6,13-dihalogen-5,14-dihydropentacene derivative represented by the following formula (I):

[Formula 3]

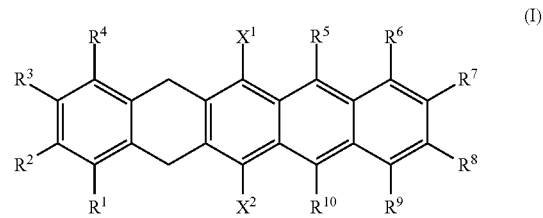

[wherein $X^1$ and $X^2$, which may be the same or different, are each independently a halogen atom, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group].

[2] The derivative according to [1] above, wherein $X^1$ and $X^2$ are each an iodine atom.

[3] The derivative according to [1] or [2] above, wherein $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ alkyl group; an optionally substituted $C_6$-$C_{20}$ aryl group or an optionally substituted silyl group.

[4] The derivative according to any one of [1] to [3] above, wherein $R^1$, $R^2$, $R^3$, $R^4$, $R^5$, $R^6$, $R^7$, $R^8$, $R^9$ and $R^{10}$ are each a hydrogen atom.

[5] A method for producing a 6,13-substituted 5,14-dihydropentacene derivative represented by the following formula (II):

[Formula 4]

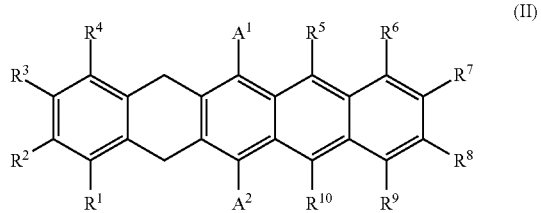

(II)

[wherein $A^1$ and $A^2$, which may be the same or different, are each independently an optionally substituted $C_1$-$C_{20}$ hydrocarbon group; an optionally substituted heteroaryl group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the heteroaryl group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group], said method comprising the step of reacting a 6,13-dihalogen-5,14-dihydropentacene derivative represented by the following formula (I):

[Formula 5]

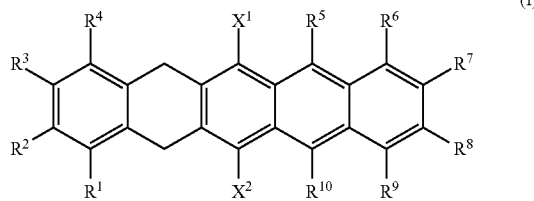

(I)

[wherein $X^1$ and $X^2$, which may be the same or different, are each independently a halogen atom, and $R^1$, $R^2$, $R^3$, $R^5$, $R^6$, $R^7$, $R^8$, $R^9$ and $R^{10}$ are the same as defined in formula (II)]

with an organometallic compound comprising $A^1$ or $A^2$ as defined in formula (II) in the presence of a transition metal catalyst.

[6] The method according to [5] above, wherein the organometallic compound is selected from the group consisting of an organolithium compound, an organomagnesium compound, an organoaluminum compound, an organozinc compound, an organoboron compound and an organosilyl compound.

[7] The method according to [5] or [6] above, wherein the organometallic compound is any of compounds represented by formulae (1) to (6):

| | |
|---|---|
| RLi | (1) |
| RMgY | (2) |
| $R_3$Al | (3) |
| RZnY | (4) |
| $RBY_2$ | (5) |
| $RSiR'_3$ | (6) |

[wherein each R, which may be the same or different, is independently $A^1$ or $A^2$ as defined in formula (II), each Y, which may be the same or different, is independently a halogen atom or a hydroxy group, and R' is a $C_1$-$C_{10}$ alkyl group].

[8] The method according to any one of [5] to [7] above, wherein the transition metal catalyst comprises a nickel complex or a palladium complex.

[9] The method according to any one of [5] to [8] above, wherein $A^1$ and $A^2$, which may be the same or different, are each independently an optionally substituted $C_1$-$C_{20}$ alkyl group, an optionally substituted $C_2$-$C_{20}$ alkenyl group, an optionally substituted $C_2$-$C_{20}$ alkynyl group, an optionally substituted $C_6$-$C_{20}$ aryl group or an optionally substituted heteroaryl group.

[10] The method according to any one of [5] to [9] above, wherein $X^1$ and $X^2$ are each an iodine atom.

[11] The method according to any one of [5] to [10] above, wherein $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ alkyl group; an optionally substituted $C_6$-$C_{20}$ aryl group or an optionally substituted silyl group.

[12] The method according to any one of [5] to [11] above, wherein $R^1$, $R^2$, $R^3$, $R^4$, $R^5$, $R^6$, $R^7$, $R^8$, $R^9$ and $R^{10}$ are each a hydrogen atom.

[13] A method for producing a 6,13-substituted pentacene derivative represented by the following formula (III):

[Formula 6]

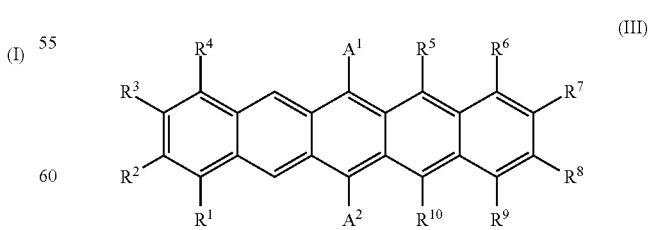

(III)

[wherein $A^1$ and $A^2$, which may be the same or different, are each independently an optionally substituted $C_1$-$C_{20}$ hydrocarbon group; an optionally substituted heteroaryl group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the amino group or the silyl group has a substituent(s), the substituent(s) is/are selected from the group consisting of a $C_1$-$C_{10}$ hydrocarbon group, a heteroaryl group, a $C_1$-$C_{10}$ alkoxy group, a $C_6$-$C_{12}$ aryloxy group, an alkoxycarbonyl group, an aryloxycarbonyl group, a carbamoyl group, an amino group, a hydroxyl group, a halogen atom and a silyl group, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group], said method comprising the steps of:

reacting a 6,13-dihalogen-5,14-dihydropentacene derivative represented by the following formula (I):

[Formula 7]

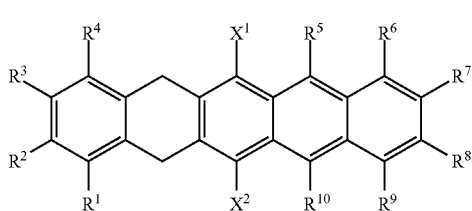

(I)

[wherein $X^1$ and $X^2$, which may be the same or different, are each independently a halogen atom, and $R^1$, $R^2$, $R^3$, $R^4$, $R^5$, $R^6$, $R^7$, $R^8$, $R^9$ and $R^{10}$ are the same as defined in formula (III)] with an organometallic compound comprising $A^1$ or $A^2$ as defined in formula (III) in the presence of a transition metal catalyst; and aromatizing the compound obtained in the above step in the presence of a dehydrogenation reagent.

[14] The method according to [13] above, wherein the organometallic compound is selected from the group consisting of an organolithium compound, an organomagnesium compound, an organoaluminum compound, an organozinc compound, an organoboron compound and an organosilyl compound.

[15] The method according to [13] or [14] above, wherein the organometallic compound is any of compounds represented by formulae (1) to (6):

$$RLi \quad (1)$$

$$RMgY \quad (2)$$

$$R_3Al \quad (3)$$

$$RZnY \quad (4)$$

$$RBY_2 \quad (5)$$

$$RSiR'_3 \quad (6)$$

[wherein each R, which may be the same or different, is independently $A^1$ or $A^2$ as defined in formula (III), each Y, which may be the same or different, is independently a halogen atom or a hydroxy group, and R' is a $C_1$-$C_{10}$ alkyl group].

[16] The method according to any one of [13] to [15] above, wherein the transition metal catalyst comprises a nickel complex or a palladium complex.

[17] The method according to any one of [13] to [16] above, wherein $A^1$ and $A^2$, which may be the same or different, are each independently an optionally substituted $C_1$-$C_{20}$ alkyl group, an optionally substituted $C_2$-$C_{20}$ alkenyl group, an optionally substituted $C_2$-$C_{20}$ alkynyl group, an optionally substituted $C_6$-$C_{20}$ aryl group or an optionally substituted heteroaryl group.

[18] The method according to any one of [13] to [17] above, wherein $X^1$ and $X^2$ are each an iodine atom.

[19] The method according to any one of [13] to [18] above, wherein $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ alkyl group; an optionally substituted $C_6$-$C_{20}$ aryl group or an optionally substituted silyl group.

[20] The method according to any one of [13] to [19] above, wherein $R^1$, $R^2$, $R^3$, $R^4$, $R^5$, $R^6$, $R^7$, $R^8$, $R^9$ and $R^{10}$ are each a hydrogen atom.

[21] A complex compound represented by the following formula (IV):

[Formula 8]

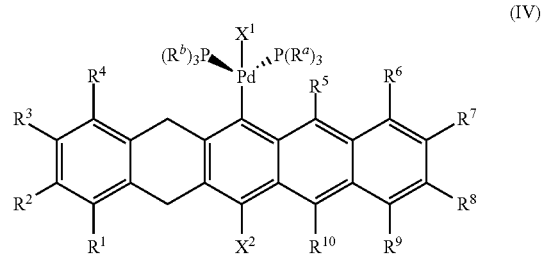

(IV)

[wherein $X^1$ and $X^2$, which may be the same or different, are each independently a halogen atom, $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group, and $R^a$ and $R^b$, which may be the same or different, are each independently a $C_1$-$C_{20}$ alkyl group or a $C_6$-$C_{20}$ aryl group].

[22] A method for producing a 6,13-substituted 5,14-dihydropentacene derivative represented by the following formula (II):

[Formula 9]

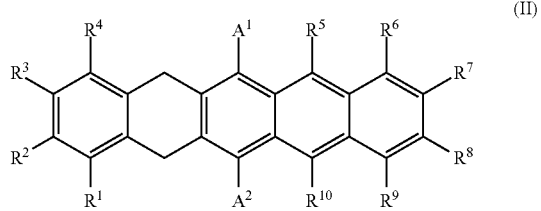

(II)

[wherein $A^1$ and $A^2$, which may be the same or different, are each independently an optionally substituted $C_1$-$C_{20}$ hydrocarbon group; an optionally substituted heteroaryl group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the heteroaryl group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group], said method comprising the step of reacting a complex compound represented by the following formula (IV):

[Formula 10]

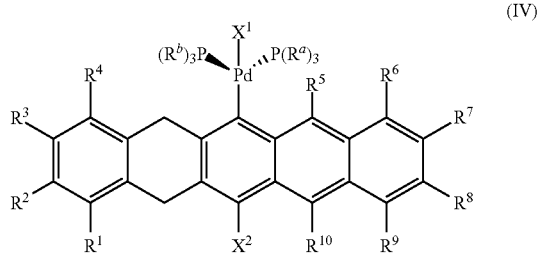

(IV)

[wherein $X^1$ and $X^2$, which may be the same or different, are each independently a halogen atom, $R^1$, $R^2$, $R^3$, $R^4$, $R^5$, $R^6$, $R^7$, $R^8$, $R^9$ and $R^{10}$ are the same as defined in formula (II), and $R^a$ and $R^b$, which may be the same or different, are each independently a $C_1$-$C_{20}$ alkyl group or a $C_6$-$C_{20}$ aryl group] with an organometallic compound comprising $A^1$ or $A^2$ as defined in formula (II).

Effect of the Invention

The present invention provides a 6,13-dihalogen-5,14-dihydropentacene derivative, which is a novel compound. When using the 6,13-dihalogen-5,14-dihydropentacene derivative of the present invention, it is possible to produce 6,13-substituted 5,14-dihydropentacene derivatives having substituents of various types at the 6- and 13-positions in a simpler manner. Moreover, it is also possible to produce 6,13-substituted pentacene derivatives having substituents of various types at the 6- and 13-positions in a simpler manner. According to the production method of the present invention, a desired compound can be produced with high selectivity. The present invention also provides an intermediate in the above production method and a method for producing a 6,13-substituted 5,14-dihydropentacene derivative using the intermediate.

BRIEF DESCRIPTION OF THE DRAWINGS

FIG. 1 shows the results of X-ray structural analysis obtained for the complex compound of the present invention (Example 7).

MODES FOR CARRYING OUT THE INVENTION

A detailed explanation will be given below of the dihalogenated dihydropentacene derivative of the present invention and a method for producing a 6,13-substituted dihydropentacene derivative using the same, as well as a 6,13-substituted pentacene derivative, etc.

[1] 6,13-Dihalogen-5,14-dihydropentacene derivative

The 6,13-dihalogen-5,14-dihydropentacene derivative of the present invention is a compound represented by the following formula (I):

[Formula 11]

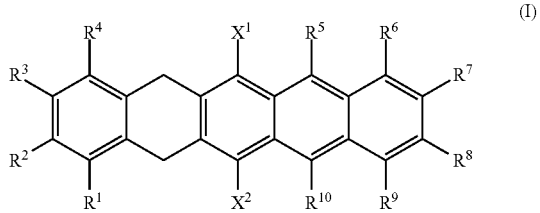

(I)

[wherein $X^1$ and $X^2$, which may be the same or different, are each independently a halogen atom, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group].

The 6,13-dihalogen-5,14-dihydropentacene derivative of the present invention has halogen atoms at the 6- and 13-positions and has any additional substituents $R^1$ to $R^{10}$ as side chains located at positions other than the 5- and 14-positions. The 6,13-dihalogen-5,14-dihydropentacene derivative of the present invention is highly soluble in organic solvents as a result of dihydro modification at the 5- and 14-positions, so that substituents of any type can be introduced with high selectivity at the 6- and 13-positions of the 6,13-dihalogen-5,14-dihydropentacene derivative of the present invention.

In the context of the present invention, the "halogen atom" includes fluorine, chlorine, bromine, and iodine. Among them, bromine or iodine is preferred.

In the context of the present invention, the hydrocarbon group in the "$C_1$-$C_{20}$ hydrocarbon group" may be saturated or unsaturated noncyclic or may be saturated or unsaturated cyclic. When the $C_1$-$C_{20}$ hydrocarbon group is noncyclic, it may be linear or branched. The "$C_1$-$C_{20}$ hydrocarbon group" includes a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_7$-$C_{20}$ alkylaryl group, a $C_7$-$C_{20}$ arylalkyl group, a $C_4$-$C_{20}$ cycloalkyl group, a $C_4$-$C_{20}$ cycloalkenyl group, a ($C_3$-$C_{10}$ cycloalkyl)$C_1$-$C_{10}$ alkyl group and so on.

In the context of the present invention, the "$C_1$-$C_{20}$ alkyl group" is preferably a $C_1$-$C_{12}$ alkyl group, more preferably a $C_1$-$C_{10}$ alkyl group, and even more preferably a $C_1$-$C_6$ alkyl group. Examples of such an alkyl group include, but are not limited to, methyl, ethyl, propyl, isopropyl, n-butyl, sec-butyl, tert-butyl, pentyl, hexyl, dodecanyl and so on.

In the context of the present invention, the "$C_2$-$C_{20}$ alkenyl group" is preferably a $C_2$-$C_{10}$ alkenyl group, and more preferably a $C_2$-$C_6$ alkenyl group. Examples of such an alkenyl group include, but are not limited to, vinyl, allyl, propenyl, isopropenyl, 2-methyl-1-propenyl, 2-methylallyl, 2-butenyl and so on.

In the context of the present invention, the "$C_2$-$C_{20}$ alkynyl group" is preferably a $C_2$-$C_{10}$ alkynyl group, and more preferably a $C_2$-$C_6$ alkynyl group. Examples of such an alkynyl group include, but are not limited to, ethynyl, propynyl, butynyl and so on. Other examples include, but are not particularly limited to, alkynyl groups having a silyl group (e.g., a triisopropylsilyl group) as a substituent.

In the context of the present invention, the "$C_4$-$C_{20}$ alkyldienyl group" is preferably a $C_4$-$C_{10}$ alkyldienyl group, and more preferably a $C_4$-$C_6$ alkyldienyl group. Examples of such an alkyldienyl group include, but are not limited to, 1,3-butadienyl and so on.

In the context of the present invention, the "$C_6$-$C_{18}$ aryl group" is preferably a $C_6$-$C_{12}$ aryl group. Examples of such an aryl group include, but are not limited to, phenyl, 1-naphthyl, 2-naphthyl, indenyl, biphenylyl, anthryl, phenanthryl and so on.

In the context of the present invention, the "$C_7$-$C_{20}$ alkylaryl group" is preferably a $C_7$-$C_{12}$ alkylaryl group. Examples of such an alkylaryl group include, but are not limited to, o-tolyl, m-tolyl, p-tolyl, 2,3-xylyl, 2,4-xylyl, 2,5-xylyl, o-cumenyl, m-cumenyl, p-cumenyl, mesityl and so on.

In the context of the present invention, the "$C_7$-$C_{20}$ arylalkyl group" is preferably a $C_7$-$C_{12}$ arylalkyl group. Examples of such an arylalkyl group include, but are not limited to, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl and so on.

In the context of the present invention, the "$C_4$-$C_{20}$ cycloalkyl group" is preferably a $C_4$-$C_{10}$ cycloalkyl group. Examples of such a cycloalkyl group include, but are not limited to, cyclopropyl, cyclobutyl, cyclopentyl, cyclohexyl and so on.

In the context of the present invention, the "$C_4$-$C_{20}$ cycloalkenyl group" is preferably a $C_4$-$C_{10}$ cycloalkenyl group. Examples of such a cycloalkenyl group include, but are not limited to, cyclopropenyl, cyclobutenyl, cyclopentenyl, cyclohexenyl and so on.

In the context of the present invention, the "$C_1$-$C_{20}$ alkoxy group" is preferably a $C_1$-$C_{10}$ alkoxy group, and more preferably a $C_1$-$C_6$ alkoxy group. Examples of the "$C_1$-$C_{20}$ alkoxy group" include, but are not limited to, methoxy, ethoxy, propoxy, butoxy, pentyloxy and so on.

In the context of the present invention, the "$C_6$-$C_{18}$ aryloxy group" is preferably a $C_6$-$C_{12}$ aryloxy group. Examples of such an aryloxy group include, but are not limited to, phenyloxy, naphthyloxy, biphenyloxy and so on.

In the context of the present invention, the "$C_1$-$C_{20}$ alkoxycarbonyl group" is preferably a $C_1$-$C_{10}$ alkoxycarbonyl group, and more preferably a $C_1$-$C_6$ alkoxycarbonyl group. Examples of such an alkoxycarbonyl group include, but are not limited to, methoxycarbonyl, ethoxycarbonyl, 2-methoxyethoxycarbonyl, t-butoxycarbonyl and so on.

In the context of the present invention, the "$C_6$-$C_{20}$ aryloxycarbonyl group" is preferably a $C_6$-$C_{12}$ aryloxycarbonyl group, and more preferably a $C_6$-$C_{10}$ aryloxycarbonyl group. Examples of such an aryloxycarbonyl group include, but are not limited to, phenoxycarbonyl, naphthoxycarbonyl, phenylphenoxycarbonyl and so on.

In the context of the present invention, the "heteroaryl group" is a monocyclic, polycyclic or condensed ring heteroaryl group containing one, two or three heteroatoms selected from an oxygen atom, a sulfur atom or a nitrogen atom. Particularly preferred are 5- or 6-membered monocyclic heteroaryl groups, as well as polycyclic heteroaryl groups in which these monocyclic heteroaryl groups are linked via a single bond. Examples of such a heteroaryl group include imidazolyl, pyridyl, furyl, pyrrolyl, thiophenyl, bithiophenyl and so on.

In the context of the present invention, if the hydrocarbon group, the heteroaryl group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group. The number of these substituents may be one or two or more.

In the context of the present invention, examples of the "optionally substituted carbamoyl group (—C(=O)NH$_2$)" include, but are not limited to, mono-$C_1$-$C_6$ alkyl-carbamoyl (e.g., methylcarbamoyl, ethylcarbamoyl), di-$C_1$-$C_6$ alkyl-carbamoyl (e.g., dimethylcarbamoyl, diethylcarbamoyl, ethylmethylcarbamoyl) and so on.

In the context of the present invention, examples of the "optionally substituted amino group" preferably include amino, dimethylamino, methylamino, methylphenylamino, phenylamino and so on.

In the context of the present invention, examples of the "optionally substituted silyl group" preferably include dimethylsilyl, diethylsilyl, trimethylsilyl, triethylsilyl, trimethoxysilyl, triethoxysilyl, diphenylmethylsilyl, triphenylsilyl, triphenoxysilyl, dimethylmethoxysilyl, dimethylphenoxysilyl, methylmethoxyphenyl, triisopropyl and so on.

In one embodiment of the present invention, it is preferred that $R^1$, $R^2$, $R^3$, $R^4$, $R^5$, $R^6$, $R^7$, $R^8$, $R^9$ and $R^{10}$, which may be the same or different, are each independently a hydrogen atom, an optionally substituted $C_1$-$C_{20}$ alkyl group or an optionally substituted $C_6$-$C_{20}$ aryl group, with a hydrogen atom being particularly preferred.

The 6,13-dihalogen-5,14-dihydropentacene derivative of the present invention can be synthesized by combining known reactions. For example, the 6,13-dihalogen-5,14-dihydropentacene derivative of the present invention can be synthesized according to the synthesis scheme shown below:

In the organometallic compound represented by $L^1L^2MY^1Y^2$, M represents a metal of Groups 3 to 5 or the lanthanide series in the periodic table. M is preferably a metal of Group 4 or the lanthanide series in the periodic table, and more preferably a metal of Group 4 in the periodic table, i.e., titanium, zirconium or hafnium.

$L^1$ and $L^2$, which may be the same or different, each independently represent an anionic ligand. Such an anionic ligand is preferably a non-localized cyclic re-coordinated ligand, a $C_1$-$C_{20}$ alkoxy group, a $C_6$-$C_{20}$ aryloxy group or a dialkylamido group. Among them, preferred is a non-localized cyclic $\eta^5$-coordinated ligand. Preferred examples of a non-localized cyclic $\eta^5$-coordinated ligand include an unsubstituted cyclopentadienyl group and a substituted cyclopentadienyl group.

[Formula 12]

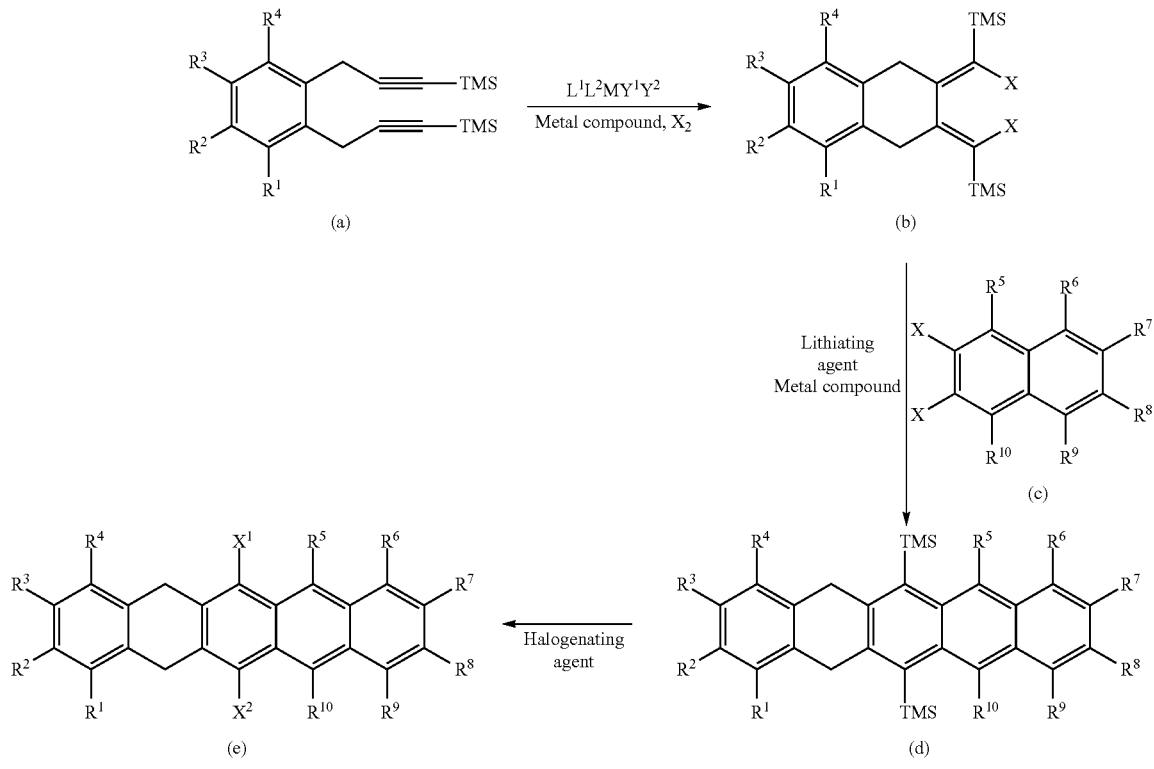

TMS: Si(CH₃)₃

[wherein $R^1$, $R^2$, $R^3$, $R^4$, $R^5$, $R^6$, $R^7$, $R^8$, $R^9$, $R^{10}$, $X^1$ and $X^2$ are as defined above; each X, which may be the same or different, independently represents a halogen atom; M represents a metal of Groups 3 to 5 or the lanthanide series in the periodic table; $L^1$ and $L^2$, which may be the same or different, each independently represent an anionic ligand, provided that $L^1$ and $L^2$ may be bridged; and $Y^1$ and $Y^2$, which may be the same or different, each independently represent a leaving group].

First, compound (a) and an organometallic compound represented by $L^1L^2MY^1Y^2$ are reacted in the presence of a metal compound and a halogen molecule $X_2$ to obtain compound (b). Formation of a dihalogenated compound from a diyne compound and an organometallic compound represented by $L^1L^2MY^1Y^2$ can be found in, e.g., Takahashi et al., Tetrahedron Letters, Vol. 38, No. 23, pp. 4099-4102 (1997), and the reaction proceeds under the same or equivalent conditions as found in this document.

Examples of a substituted cyclopentadienyl group include methylcyclopentadienyl, ethylcyclopentadienyl, isopropylcyclopentadienyl, n-butylcyclopentadienyl, t-butylcyclopentadienyl, dimethylcyclopentadienyl, diethylcyclopentadienyl, diisopropylcyclopentadienyl, di-t-butylcyclopentadienyl, tetramethylcyclopentadienyl, indenyl, 2-methylindenyl, 2-methyl-4-phenylindenyl, tetrahydroindenyl, benzoindenyl, fluorenyl, benzofluorenyl, tetrahydrofluorenyl and octahydrofluorenyl.

In these non-localized cyclic $\eta^5$-coordinated ligands, one or more atoms in the non-localized cyclic π system may be replaced with heteroatoms. These ligands may comprise, in addition to hydrogens, one or more heteroatoms such as elements of Group 14 in the periodic table and/or elements of Groups 15, 16 and 17 in the periodic table.

Such a non-localized cyclic $\eta^5$-coordinated ligand, e.g., a cyclopentadienyl group may be bridged to the central metal via one or more bridging ligands which may be cyclic. Examples of a bridging ligand include $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$.

$Y^1$ and $Y^2$, which may be the same or different, each independently represent a leaving group. Examples of a leaving group include halogen atoms (e.g., F, Cl, Br, I); $C_1$-$C_{20}$ alkyl groups (e.g., a n-butyl group); $C_6$-$C_{20}$ aryl groups (e.g., a phenyl group) and so on. Among them, halogen atoms are preferred.

It should be noted that when a dihalogeno compound is used as an organometallic compound represented by $L^1L^2MY^1Y^2$, as exemplified by bis(cyclopentadienyl)dichlorozirconium; bis(methylcyclopentadienyl)dichlorozirconium; bis(butylcyclopentadienyl)dichlorozirconium; bis(indenyl)dichlorozirconium; bis(fluorenyl)dichlorozirconium; (indenyl)(fluorenyl)dichlorozirconium; bis(cyclopentadienyl)dichlorotitanium; (dimethylsilanediyl)bis(indenyl)dichlorozirconium; (dimethylsilanediyl)bis(tetrahydroindenyl)dichlorozirconium; (dimethylsilanediyl)(indenyl)dichlorozirconium; (dimethylsilanediyl)bis(2-methylindenyl)dichlorozirconium; (dimethylsilanediyl)bis(2-ethylindenyl)dichlorozirconium; (dimethylsilanediyl)bis(2-methyl-4,5-benzoindenyl)dichlorozirconium; (dimethylsilanediyl)bis(2-ethyl-4,5-benzoindenyl)dichlorozirconium; (dimethylsilanediyl)bis(2-methyl-4-phenylindenyl)dichlorozirconium; (dimethylsilanediyl)bis(2-ethyl-4-phenylindenyl)dichlorozirconium; (dimethylsilanediyl)bis(2-methyl-4,6-diisopropylindenyl)dichlorozirconium, etc., it is preferred that such a dihalogeno compound is reduced with a strong base of an alkali metal (e.g., sodium), an alkaline earth metal (e.g., magnesium) or the like or converted into a dialkyl form before use.

The amount of the organometallic compound represented by $L^1L^2MY^1Y^2$ to be used is preferably 0.1 to 10 moles, more preferably 0.5 to 3 moles, and even more preferably 0.5 to 2 moles, relative to 1 mole of compound (a).

A metal compound preferred for use in the reaction is a metal compound of Groups 4 to 15 in the periodic table. Such a metal compound may be in a salt form such as CuCl or may be an organometallic complex.

Examples of a salt used for this purpose include metal salts, as exemplified by $CuX$, $NiX_2$, $PdX_2$, $ZnX_2$, $CrX_2$, $CrX_3$, $CoX_2$ or $BiX_3$ (wherein X represents a halogen atom such as a chlorine atom, a bromine atom, etc.).

Organometallic complexes preferred for use are those in which the central metal of Groups 3 to 11 in the periodic table, preferably the central metal of Groups 6 to 11 in the periodic table is coordinated with ligands such as phosphine, aromatic amines (e.g., pyridine, bipyridine), halogen atoms, etc. The central metal preferably allows so-called coordination with 4 to 6 ligands, and is more preferably a metal of Group 10 in the periodic table. Phosphine may be of any form, such as triphenylphosphine, methyldiphenylphosphine, etc. Examples of organometallic complexes include bis(triphenylphosphine)dichloronickel, dichloro(2,2'-bipyridine)nickel, and $PdCl_2$(2,2'-bipyridine). Particularly desired are nickel complexes and palladium complexes, which are used as catalysts for cross-coupling reactions.

The amount of the metal compound to be used is preferably 0.0001 to 10 moles, more preferably 0.001 to 3 moles, and even more preferably 0.01 to 1 mole, relative to 1 mole of compound (a).

Examples of a halogen molecule $X_2$ include fluorine, chlorine, bromine, and iodine molecules, with an iodine molecule being preferred. The halogen molecule $X_2$ is preferably used in an equimolar to slightly molar excess amount, relative to 1 mole of compound (a).

The reaction is preferably performed in the temperature range of −80° C. to 200° C., more preferably in the temperature range of −50° C. to 100° C., and particularly preferably in the temperature range of −20° C. to 80° C. Although the reaction is desirably performed under normal pressure, it may be operated under elevated or reduced pressure in some cases. Moreover, the reaction may be accomplished in a continuous or batch mode through one or more steps.

As a reaction solvent, an aliphatic or aromatic solvent may be used, as exemplified by ethers (e.g., tetrahydrofuran, diethyl ether); halogenated hydrocarbons (e.g., methylene chloride); halogenated aromatic hydrocarbons (e.g., o-dichlorobenzene); amides (e.g., N,N-dimethylformamide), sulfoxides (e.g., dimethyl sulfoxide). Alternatively, an aromatic hydrocarbon such as benzene, toluene or xylene may be used as an aromatic solvent.

Next, compound (b) is treated with a lithiating agent, followed by coupling reaction with compound (c) in the presence of a metal compound to obtain compound (d).

During the above reaction, compound (d) can be obtained when compound (c) is reacted in an equimolar to slightly molar excess amount, relative to 1 mole of compound (b). Compound (c) is known and can be easily synthesized by referring to, e.g., Takahashi et al., J. Am. Chem. Soc., 2002, 124 (4), pp 576. Alternatively, a commercially available product may also be used.

As a lithiating agent, preferred is a $C_1$-$C_{20}$ hydrocarbon lithium such as alkyllithium, aryllithium, etc. For example, preferred for use is a $C_1$-$C_6$ alkyllithium such as butyllithium or a $C_6$-$C_{20}$ aryllithium such as phenyllithium.

As a metal compound, any of the same metal compounds as listed above may be used. Among them, preferred are metal salts such as $CuX$, $NiX_2$, $PdX_2$, $ZnX_2$, $CrX_2$, $CrX_3$, $CoX_2$ or $BiX_3$ (wherein X represents a halogen atom such as a chlorine atom, a bromine atom, etc.). The amount of the metal compound to be used is preferably 0.01 to 100 moles, more preferably 0.1 to 10 moles, and even more preferably 0.1 to 3 moles, relative to 1 mole of the dilithiated form.

This coupling reaction may preferably be accomplished in the presence of a stabilizing agent such as N,N'-dimethylpropyleneurea, hexamethylphosphoamide, etc. The amount of the stabilizing agent to be used is preferably 0.01 to 100 moles, more preferably 0.1 to 10 moles, and even more preferably 0.1 to 3 moles, relative to 1 mole of the dilithiated form.

The reaction temperature is preferably −80° C. to 200° C., more preferably −50° C. to 100° C., and even more preferably −20° C. to 80° C. Moreover, although the reaction is desirably performed under normal pressure, it may be operated under elevated or reduced pressure in some cases. The reaction may be accomplished in a continuous or batch mode through one or more steps. As a reaction solvent, an aliphatic or aromatic solvent may be used. For specific examples of the reaction solvent, reference may be made to those illustrated in the above step.

Subsequently, compound (d) is treated with a halogenating agent to obtain compound (e) according to the present invention.

A halogenating agent may be exemplified by N-chlorosuccinimide (NCS), N-bromosuccinimide (NBS), N-iodosuccinimide (NIS), iodine monochloride, etc.

The reaction temperature is preferably −78° C. to 150° C., more preferably −78° C. to 50° C., and even more preferably −78° C. to 30° C. Moreover, although the reaction is desirably performed under normal pressure, it may be operated under elevated or reduced pressure in some cases. As a reaction solvent, an aliphatic or aromatic solvent may be used. For specific examples of the reaction solvent, reference may be made to those illustrated in the above step.

For example, compound (e) can be obtained when the halogenating agent is reacted in an equimolar to slightly molar excess amount, relative to 1 mole of compound (d), in a solvent such as dichloromethane.

After completion of the reaction in each step, the reaction mixture may optionally be treated by isolation and purification techniques used in common organic synthesis reactions to thereby obtain the desired compound in each step.

[2] Method for producing a 6,13-substituted 5,14-dihydropentacene derivative Next, an explanation will be given of the method of the present invention for producing a 6,13-substituted 5,14-dihydropentacene derivative. The method of the present invention for producing a 6,13-substituted 5,14-dihydropentacene derivative is a method for producing a 6,13-substituted 5,14-dihydropentacene derivative represented by the following formula (II):

[Formula 13]

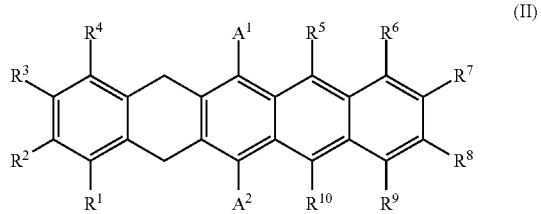

(II)

[wherein $A^1$ and $A^2$, which may be the same or different, are each independently an optionally substituted $C_1$-$C_{20}$ hydrocarbon group; an optionally substituted heteroaryl group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the heteroaryl group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group], said method comprising the step of reacting a 6,13-dihalogen-5,14-dihydropentacene derivative represented by the following formula (I):

[Formula 14]

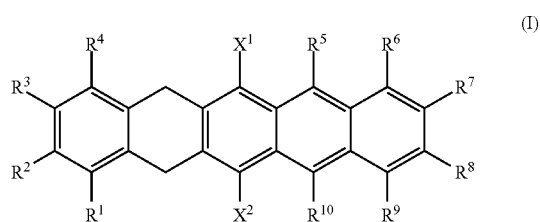

(I)

[wherein $X^1$ and $X^2$, which may be the same or different, are each independently a halogen atom, and $R^1$, $R^2$, $R^3$, $R^4$, $R^5$, $R^6$, $R^7$, $R^8$, $R^9$ and $R^{10}$ are the same as defined in formula (II)] with an organometallic compound comprising $A^1$ or $A^2$ as defined in formula (II) in the presence of a transition metal catalyst.

As described above, in the present invention, a 6,13-dihalogen-5,14-dihydropentacene derivative represented by formula (I) is reacted with an organometallic compound comprising $A^1$ or $A^2$ through coupling reaction in the presence of a transition metal catalyst to thereby produce a desired compound (i.e., a compound represented by formula (II)). As a 6,13-dihalogen-5,14-dihydropentacene derivative represented by formula (I), those illustrated above in "A. 6,13-Dihalogen-5,14-dihydropentacene derivative" can be used.

Any organometallic compound comprising $A^1$ or $A^2$ may be used as long as it is capable of providing $A^1$ and $A^2$ at the 6- and 13-positions, respectively, of the compound represented by formula (I) through cross-coupling reaction, and such an organometallic compound also encompasses compounds of semi-metals such as silicon and boron. Examples include organolithium compounds, organomagnesium compounds, organoaluminum compounds, organozinc compounds, organoboron compounds and organosilyl compounds, etc.

For example, as an organometallic compound comprising $A^1$ or $A^2$ for use in this reaction, compounds represented by the following formulae (1) to (6) are preferred for use:

| | |
|---|---|
| RLi | (1) |
| RMgY | (2) |
| $R_3$Al | (3) |
| RZnY | (4) |
| $RBY_2$ | (5) |
| $RSiR'_3$ | (6) |

[wherein each R, which may be the same or different, is independently $A^1$ or $A^2$ as defined in formula (II), each Y, which may be the same or different, is independently a halogen atom or a hydroxy group, and R' is a $C_1$-$C_{10}$ alkyl group].

Among these compounds, $R_3$Al, RZnCl, RMgBr, RB(OH)$_2$, RSi(CH$_3$)$_3$ or RSi(CH(CH$_3$)$_2$)$_3$ is particularly preferred for use as an organometallic compound. These organometallic compounds comprising $A^1$ or $A^2$ may be used either alone or in combination, as long as the object of the present invention is not impaired. When the substituents $A^1$ and $A^2$ to be introduced are of different types, it is preferable to use an organometallic compound comprising $A^1$ and an organometallic compound comprising $A^2$.

During the above reaction, the desired compound (i.e., the compound represented by formula (II)) can be obtained when the organometallic compound is reacted in an equal to slightly excess amount (preferably 1 to 10 equivalents, more preferably 1 to 5 equivalents), relative to 1 mole of the compound represented by formula (I).

The above reaction is accomplished in the presence of a catalyst containing a catalytic amount of a transition metal (e.g., Pd, Cu, Ni or W) (i.e., a transition metal catalyst). As a transition metal catalyst, preferred is a Pd(0) organic complex, a Pd(II) salt or an organic complex thereof. Specific examples include palladium/carbon, tetrakis(triphenylphosphine)palladium, palladium(II) chloride, dichlorobis(triphenylphosphine)nickel(II), dichlorobis(triphenylphosphine)palladium(II), dichloro(2,2'-bipyridine)nickel and so on.

The amount of the transition metal catalyst to be used is preferably 0.5 moles or less, more preferably 0.0001 to 0.5 moles, and even more preferably 0.001 to 0.2 moles, relative to 1 mole of the compound represented by formula (I).

The reaction temperature is preferably −80° C. to 200° C., more preferably −50° C. to 100° C., and even more preferably −20° C. to 80° C. Moreover, although the reaction is desirably performed under normal pressure, it may be operated under elevated or reduced pressure in some cases. The reaction may be accomplished in a continuous or batch mode through one or more steps.

As a reaction solvent, an aliphatic or aromatic solvent may be used, as exemplified by ethers (e.g., tetrahydrofuran, diethyl ether); halogenated hydrocarbons (e.g., methylene chloride); halogenated aromatic hydrocarbons (e.g., o-dichlorobenzene); amides (e.g., N,N-dimethylformamide), sulfoxides (e.g., dimethyl sulfoxide). Alternatively, an aromatic hydrocarbon such as benzene, toluene or xylene may be used as an aromatic solvent.

After completion of the reaction, the reaction mixture may optionally be treated by isolation and purification techniques used in common organic synthesis reactions to thereby obtain the desired compound, i.e., a 6,13-substituted 5,14-dihydropentacene derivative. This 6,13-substituted 5,14-dihydropentacene derivative may be aromatized in a routine manner, as described later, to thereby easily obtain a 6,13-substituted pentacene derivative.

According to the present invention, the desired compound can be obtained with high selectivity by means of characteristics of cross-coupling reaction.

In one embodiment of the present invention, it is preferred that $A^1$ and $A^2$, which may be the same or different, are each independently an optionally substituted $C_1$-$C_{20}$ alkyl group, an optionally substituted $C_2$-$C_{20}$ alkenyl group, an optionally substituted $C_2$-$C_{20}$ alkynyl group, an optionally substituted $C_6$-$C_{20}$ aryl group or an optionally substituted heteroaryl group.

Moreover, in one embodiment of the present invention, it is preferred that $X^1$ and $X^2$ are each an iodine atom.

Further, in one embodiment of the present invention, it is preferred that $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ alkyl group; an optionally substituted $C_6$-$C_{20}$ aryl group or an optionally substituted silyl group.

Furthermore, in one embodiment of the present invention, it is preferred that $R^1$, $R^2$, $R^3$, $R^4$, $R^5$, $R^6$, $R^7$, $R^8$, $R^9$ and $R^{10}$ are each a hydrogen atom.

In one embodiment of the present invention, the above 6,13-dihalogen-5,14-dihydropentacene derivative represented by formula (I) may be reacted with an organometallic complex to form a complex compound represented by formula (IV) shown below, followed by reaction with an organometallic compound comprising $A^1$ or $A^2$ to produce the desired compound:

[Formula 15]

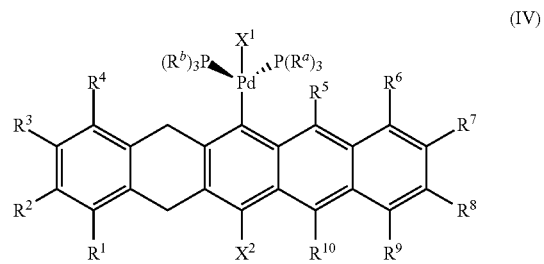

(IV)

[wherein $X^1$ and $X^2$, which may be the same or different, are each independently a halogen atom, $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group, and $R^a$ and $R^b$, which may be the same or different, are each independently a $C_1$-$C_{20}$ alkyl group or a $C_6$-$C_{20}$ aryl group].

As an organometallic complex, preferred is a Pd(0) organic complex, a Pd(II) salt or an organic complex thereof. Examples preferably include tetrakis(triphenylphosphine)palladium, dichlorobis(triphenylphosphine)palladium(II) and so on.

A desired compound (i.e., a compound represented by formula (IV)) can be obtained when the organometallic complex is reacted in an equal to slightly excess amount, relative to 1 mole of the compound represented by formula (I). Moreover, the resulting compound may further be reacted with, e.g., trialkylphosphine or triarylphosphine to thereby obtain a desired compound (i.e., a compound represented by formula (IV)).

As a reaction solvent, an aliphatic or aromatic solvent may be used, as exemplified by ethers (e.g., tetrahydrofuran, diethyl ether); halogenated hydrocarbons (e.g., methylene chloride); halogenated aromatic hydrocarbons (e.g., o-dichlorobenzene); amides (e.g., N,N-dimethylformamide), sulfoxides (e.g., dimethyl sulfoxide). Alternatively, an aromatic hydrocarbon such as benzene, toluene or xylene may be used as an aromatic solvent.

After completion of the reaction, the reaction mixture may optionally be treated by isolation and purification techniques used in common organic synthesis reactions to thereby obtain the desired compound (i.e., the compound represented by formula (IV)).

The resulting compound represented by formula (IV) may be reacted with an organometallic compound comprising $A^1$ or $A^2$ as described above through cross-coupling reaction to thereby obtain the 6,13-substituted 5,14-dihydropentacene derivative represented by formula (II).

The amount of the organometallic compound comprising $A^1$ or $A^2$ to be used is preferably an equal to slightly excess amount relative to 1 mole of the compound represented by formula (IV), more preferably 1 to 10 equivalents, and even more preferably 1 to 5 equivalents.

As a reaction solvent, the same solvent as used in the above reaction may also be used in this reaction.

[3] Method for producing a 6,13-substituted pentacene derivative

Next, an explanation will be given of the method of the present invention for producing a 6,13-substituted pentacene derivative. The method of the present invention for producing a 6,13-substituted pentacene derivative is a method for producing a 6,13-substituted pentacene derivative represented by the following formula

[Formula 16]

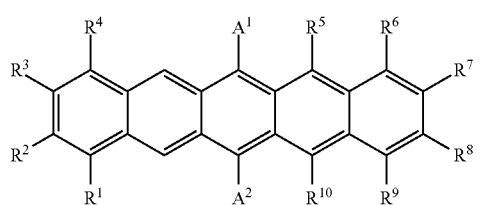

(III)

[wherein $A^1$ and $A^2$, which may be the same or different, are each independently an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an alkoxycarbonyl group, an aryloxycarbonyl group, a carbamoyl group, an amino group, a hydroxyl group, a halogen atom and a silyl group, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group], said method comprising the steps of:
reacting a 6,13-dihalogen-5,14-dihydropentacene derivative represented by the following formula (I):

[Formula 17]

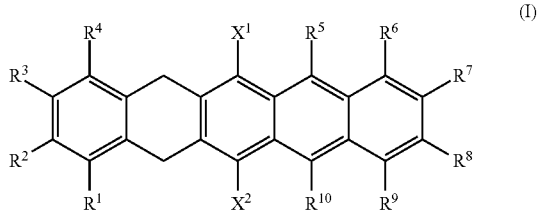

(I)

[wherein $X^1$ and $X^2$, which may be the same or different, are each independently a halogen atom, and $R^1$, $R^2$, $R^3$, $R^4$, $R^5$, $R^6$, $R^7$, $R^8$, $R^9$ and $R^{10}$ are the same as defined in formula (III)] with an organometallic compound comprising $A^1$ or $A^2$ as defined in formula (III) in the presence of a transition metal catalyst; and aromatizing the compound obtained in the above step in the presence of a dehydrogenation reagent.

The step of reacting a 6,13-dihalogen-5,14-dihydropentacene derivative represented by formula (I) with an organometallic compound comprising $A^1$ or $A^2$ is as described above in "B. Method for producing a 6,13-substituted 5,14-dihydropentacene derivative."

In the present invention, a desired pentacene derivative whose 6- and 13-positions are substituted can be obtained when the 6,13-substituted 5,14-dihydropentacene derivative represented by formula (II) obtained in the above step is aromatized in the presence of a dehydrogenation reagent.

In one embodiment of the present invention, it is preferred that a lithiating agent is used as a dehydrogenation reagent.

As a lithiating agent, preferred is a $C_1$-$C_{20}$ hydrocarbon lithium such as alkyllithium, aryllithium, etc. For example, preferred for use is a $C_1$-$C_6$ alkyllithium such as butyllithium or a $C_6$-$C_{20}$ aryllithium such as phenyllithium. Such a lithiating agent is used in an amount of preferably 0.1 to 10 equivalents, more preferably 0.5 to 5 equivalents, and even more preferably 1 to 3 equivalents of the above compound represented by formula (II).

The lithiating agent is preferably used together with an activator for the lithiating agent. Preferred activators are tertiary amines including N,N,N',N'-tetraalkylalkylenectiamines such as N,N,N',Nt-tetramethylethylenediamine (TMEDA). An alkyllithium appears to be present in the form of an oligomer such as a tetramer in a solution. In the presence of a tertiary amine, nitrogen atoms in the amine will be coordinated to the lithium atom in the alkyllithium to thereby disrupt the oligomer structure. As a result of this, the lithium atom in the alkyllithium will be exposed to the solution, resulting in improved reactivity. The amount of the activator to be used may be determined as appropriate, depending on the type thereof, etc.

As a reaction solvent, a nonpolar organic solvent is preferably used. For example, an alkane (e.g., hexane) or an aromatic compound (e.g., benzene) is preferred for use.

The reaction temperature is preferably 0° C. to 200° C., more preferably 20° C. to 100° C., and even more preferably 30° C. to 80° C.

In another embodiment of the present invention, a quinone compound represented by the following formula is used as the above dehydrogenation reagent:

[Formula 18]

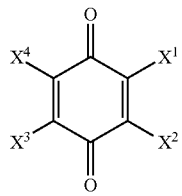

[wherein $X^1$, $X^2$, $X^3$ and $X^4$, which may be the same or different, are each independently a halogen atom or a cyano group].

For example, $X^1$, $X^2$, $X^3$ and $X^4$ may each be a chlorine atom. Namely, the above quinone compound may be chloranil. Alternatively, $X^1$ and $X^2$ may each be a cyano group, while $X^3$ and $X^4$ may each be a chlorine atom. Namely, the above quinone compound may be 2,3-dichloro-5,6-dicyanoquinone. $X^1$, $X^2$, $X^3$ and $X^4$ may each be a cyano group. Namely, the above quinone compound may be 2,3,5,6-tetracyanoquinone.

To prevent such by-product formation, the above quinone compound is used in an amount of preferably 0.9 to 1.2 equivalents, more preferably 0.9 to 1.15 equivalents, and even more preferably 0.95 to 1.05 equivalents of the above compound represented by formula (II).

As a reaction solvent, preferred is an aromatic compound such as benzene.

The reaction temperature is preferably −80° C. to 200° C., more preferably 0° C. to 100° C., and even more preferably 10° C. to 80° C. If desired, the reaction may be allowed to proceed under light shielding conditions.

In yet another embodiment of the present invention, the above dehydrogenation reagent preferably comprises palladium. For example, palladium supported on carbon (e.g., activated carbon), which is commercially available as so-called palladium on carbon, may preferably be used for this purpose. Pd/C is a catalyst widely used for dehydrogenation and may also be used in the present invention as in conventional cases. The reaction temperature is 200° C. to 500° C., by way of example. It should be noted that the reaction temperature may be determined as appropriate, depending on various conditions such as starting materials, etc.

After completion of the reaction, the reaction mixture may optionally be treated by isolation and purification techniques used in common organic synthesis reactions to thereby obtain the desired compound, i.e., a 6,13-substituted pentacene derivative. For details of the aromatization step, reference may be made to WO01/064611 and JP 2004-331534A.

EXAMPLES

The present invention will be further described by way of the following examples, which are not intended to limit the scope of the present invention.

All the reactions were performed under a nitrogen atmosphere, unless otherwise specified. Tetrahydrofuran (THF) was dried over a sodium/benzophenone system before use. Commercially available reagents were used directly without purification, unless otherwise specified. NMR yields were each determined by using mesitylene as an internal standard.

Example 1

Preparation of 6,13-diiodo-5,14-dihydropentacene derivative (1)

Step 1: Preparation of 2,3-bis-(iodotrimethylsilylmethylene)-1,2,3,4-tetrahydronaphthalene

[Formula 19]

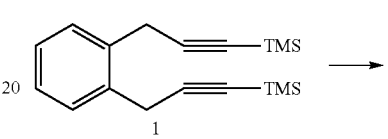

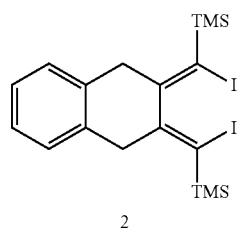

Bis(η$^5$-cyclopentadienyl)dichlorozirconium (365 mg, 1.25 mmol) was dissolved in THF (15 ml). To this solution, n-butyllithium (1.56 M in hexane, 1.60 mL, 2.5 mmol) was added at −78° C., and this mixture was stirred for 15 minutes. The resulting solution was kept at −40° C. for 30 minutes and then cooled again to −78° C. After 15 minutes passed, this solution was mixed with compound 1 (298 mg, 1.0 mmol) and returned to room temperature. After stirring for 3 hours, the reaction mixture was mixed with CuCl (99 mg, 1.0 mmol) and I$_2$ (508 mg, 2.0 mmol) at 0° C., returned again to room temperature and then allowed to stand for 3 hours. After cooling to 0° C., the resulting reaction mixture was quenched with 3 N HCl, and the reaction product was extracted with ethyl acetate. The organic layer was washed with water, saturated aqueous sodium bicarbonate and aqueous sodium chloride, and then dried over anhydrous magnesium sulfate. After distilling off the solvent, the resulting brown viscous oil was purified by silica gel chromatography (hexane:triethylamine=100:1) to give the titled compound (compound 2) as a light-yellow solid (397 mg, yield: 72%).

2: $^1$H NMR (CDCl$_3$, Me$_4$Si) δ: 0.33 (s, 18H), 3.60 (d, J=16.5 Hz, 2H), 3.91 (d, J=16.5 Hz, 2H), 7.04-7.07 (m, 2H), 7.15-7.18 (m, 2H); $^{13}$C NMR (CDCl$_3$, Me$_4$Si) δ: 1.7, 38.5, 104.9, 126.5, 128.3, 135.8, 160.3

Step 2: Preparation of 6,13-bis(trimethylsilyl)-5,14-dihydropentacene

[Formula 20]

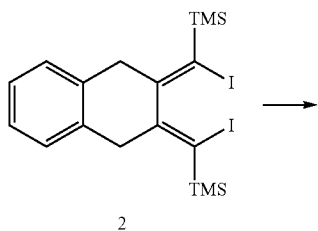

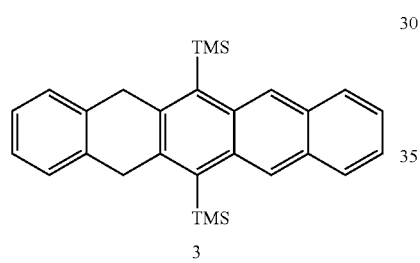

Compound 2 obtained in step 1 (552 mg, 1.0 mmol) was dissolved in THF (15 ml). To this solution, t-butyllithium (1.76 M in n-pentane, 2.27 mL, 4.0 mmol) was slowly added at −78° C., and this mixture was stirred for 15 minutes. The resulting solution was kept at −40° C. for 30 minutes and then cooled again to −78° C. After 15 minutes passed, this solution was mixed with CuCl (198 mg, 2.0 mmol) and DMPU (0.36 mL, 3.0 mmol), followed by stirring at 0° C. for 0.5 hours. Then, to this reaction mixture, 2,3-diiodonaphthalene (760 mg, 2.0 mmol) was added and heated at 50° C. for 12 hours. The reaction mixture was cooled to 0° C. and then quenched with 3 N HCl, and the reaction product was extracted with hexane. The organic layer was washed with saturated aqueous sodium bicarbonate and aqueous sodium chloride, and then dried over anhydrous magnesium sulfate. The resulting solution was concentrated under reduced pressure, and the residue was purified by silica gel chromatography (hexane:ethyl acetate:triethylamine=50:1:1) to give the titled compound (compound 3) as a yellow solid (169 mg, yield: 40%).

3: $^1$H NMR (CDCl$_3$, Me$_4$Si) δ: 0.70 (s, 18H), 4.21 (s, 4H), 7.20-7.23 (m, 2H), 7.32-7.35 (m, 2H), 7.41-7.44 (m, 2H), 7.92-7.96 (m, 2H), 8.69 (s, 2H); $^{13}$C NMR (CDCl$_3$, Me$_4$Si) δ: 4.3, 39.2, 125.0, 126.5, 126.6, 126.9, 128.0, 130.1, 134.7, 135.5, 138.1, 143.9;

HRMS (EI) C$_{28}$H$_{32}$Si$_2$: Calculated: 424.2043. Found: 424.2037.

Step 3: Preparation of 6,13-diiodo-5,14-dihydropentacene derivative

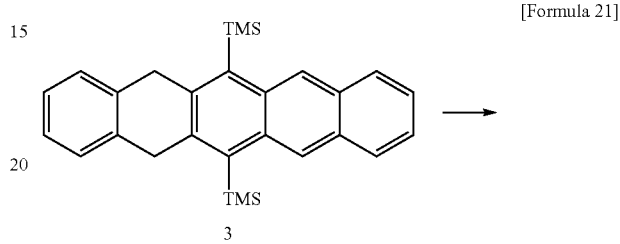

[Formula 21]

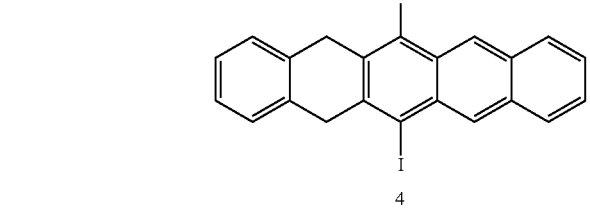

Compound 3 obtained in step 2 (424 mg, 1.0 mmol) was dissolved in dichloromethane (5 mL). To this solution, ICl (1.0 M in dichloromethane, 2.0 mL, 2.0 mmol) was slowly added at −78° C. After stirring at −78° C. for 3 hours, the resulting reaction mixture was quenched with saturated aqueous sodium thiosulfate, and the reaction product was extracted with chloroform. The organic layer was washed with aqueous sodium chloride. After removal of the solvent, the residue was washed with methanol. The generated precipitates were recovered, and the residue was purified by silica gel chromatography (chloroform) to give the titled compound (compound 4) as a brown liquid (119 mg, yield: 23%).

4: $^1$H NMR (CDCl$_3$, Me$_4$Si) δ: 4.47 (s, 4H), 7.25-7.29 (m, 2H), 7.43-7.44 (m, 2H), 7.52-7.55 (m, 2H), 8.09-8.12 (m, 2H), 8.85 (s, 2H); $^{13}$C NMR (CDCl$_3$, Me$_4$Si) δ: 45.5, 106.7, 126.5, 126.9, 127.2, 128.1, 132.1, 132.8, 133.0, 136.3, 139.8;

HRMS (EI) $C_{22}H_{14}I_2$: Calculated: 531.9185. Found: 531.9199.

Example 2

Preparation of 6,13-diiodo-5,14-dihydropentacene derivative (2)

[Formula 22]

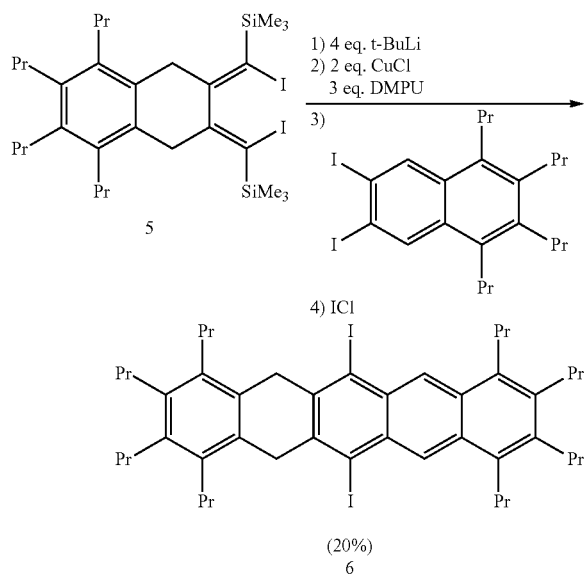

The same procedure as shown in Example 1 was repeated using a substituted diiododiene and a substituted diiodonaphthalene, resulting in a 6,13-diiodo-5,14-dihydropentacene derivative having eight substituents. The yield was 20%.

6: $^1$H NMR ($C_6D_6$) δ: 1.03 (t, J=7 Hz, 6H), 1.06 (t, J=7 Hz, 6H), 1.22 (t, J=7 Hz, 6H), 1.29 (t, J=7 Hz, 6H), 1.63-1.76 (m, 12H), 1.97-2.01 (m, 4H), 2.67-2.71 (m, 4H), 2.84-2.94 (m, 8H), 3.33-3.37 (m, 4H), 4.31 (s, 4H), 9.28 (s, 2H); $^{13}$C NMR ($C_6D_6$) δ: 15.21, 15.24, 15.4, 15.5, 24.9, 25.3, 25.6, 25.7, 32.3, 32.71, 32.74, 33.3, 42.6, 106.6, 130.6, 131.5, 131.9, 133.9, 134.4, 135.4, 137.1, 137.8, 141.5;

HRMS (EI) Calculated: $C_{46}H_{62}I_2$: 868.2941. Found: 868.2947.

Example 3

Preparation of 6,13-dimethyl-5,14-dihydropentacene

[Formula 23]

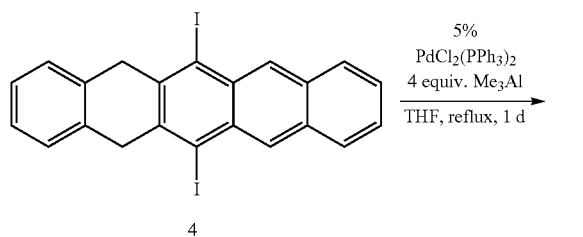

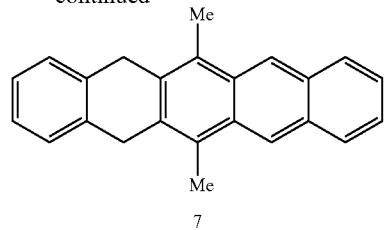

Compound 4 obtained in Example 1 (161 mg, 0.30 mmol) and $PdCl_2(PPh_3)_2$ (10 mg, 0.0015 mmol) were dissolved in THF (10 mL). To this solution, $Me_3Al$ (1.0 M in hexane, 1.2 mL, 1.2 mmol) was added, and the resulting mixture was heated under reflux for 1 hour. The reaction mixture was cooled to room temperature and then quenched with 3 N HCl, and the reaction product was extracted with chloroform. After removal of the solvent, the residue was purified by silica gel chromatography (hexane:ethyl acetate=10:1) to give the titled compound (compound 7) as a light-yellow solid (76 mg, isolated yield: 82%).

7: $^1$H NMR ($CDCl_3$, $Me_4Si$, 600 MHz) δ: 2.78 (s, 6H), 4.10 (s, 4H), 7.14-7.16 (m, 2H), 7.28-7.30 (m, 2H), 7.34-7.36 (m, 2H), 7.92-7.93 (m, 2H), 8.50 (s, 2H); $^{13}$C NMR ($CDCl_3$, $Me_4Si$) δ: 15.1, 34.4, 123.0, 125.1, 126.4, 127.1, 127.3, 128.3, 130.8, 131.0, 132.6, 137.3.

HRMS (EI) $C_{24}H_{20}$: Calculated: 308.1565. Found: 308.1565.

Example 4

Preparation of 6,13-diethyl-5,14-dihydropentacene

[Formula 24]

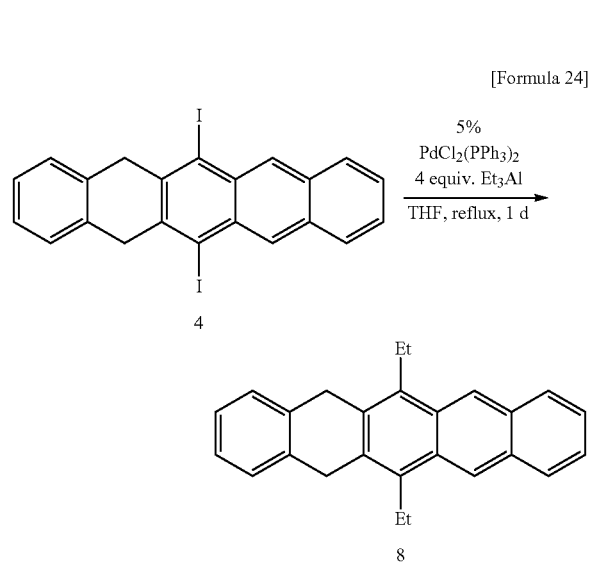

The same reaction as conducted in Example 3 was repeated except for using $Et_3Al$ instead of $Me_3Al$, resulting in the titled compound (compound 8) as a yellow solid (NMR yield: 74%, isolated yield: 65%).

8: $^1$H NMR ($CDCl_3$, $Me_4Si$, 600 MHz) δ: 1.40 (t, J=7 Hz, 6H), 3.38 (q, J1,2=7.8 Hz, J1,3=15.6 Hz, 4H), 4.15 (s, 4H), 7.22-7.23 (m, 2H), 7.37-7.38 (m, 2H), 7.41-7.43 (m, 2H), 8.00-8.01 (m, 2H), 8.62 (s, 2H); $^{13}$C NMR ($CDCl_3$, $Me_4Si$) δ: 15.0, 22.0, 34.0, 122.9, 125.0, 126.5, 127.0, 128.4, 129.9, 131.0, 132.4, 133.4, 137.9.

HRMS (EI) C$_{26}$H$_{24}$: Calculated: 336.1878. Found: 336.1868.

Example 5

Preparation of 6,13-diphenyl-5,14-dihydropentacene

[Formula 25]

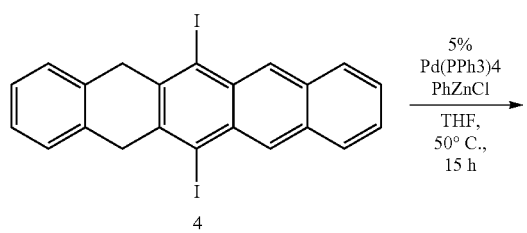

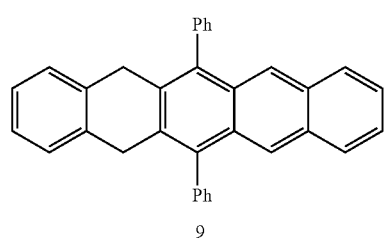

Aryllithium (0.2 mL, 0.4 mmol) and dry zinc chloride (52 mg, 0.4 mmol) were reacted in THF (2 mL) to prepare an arylzinc reagent. To the arylzinc reagent thus prepared, compound 4 obtained in Example 1 (50 mg, 0.09 mmol) and a palladium(0) catalyst (Pd(PPh$_3$)$_4$, 5 mg, 0.0045 mmol) were then added, and this mixture was heated at 50° C. for 15 hours. The reaction mixture was cooled to room temperature and then quenched with 3 N HCl, and the reaction product was extracted with chloroform. The organic layer was washed with water, saturated aqueous sodium bicarbonate and aqueous sodium chloride, and then dried over anhydrous magnesium sulfate. The solvent was distilled off under reduced pressure, and the resulting residue was purified by GPC to give the titled compound (compound 9) as a yellow solid (13 mg, yield: 34%).

9: $^1$H NMR (CDCl$_3$, Me$_4$Si, 400 MHz)) δ: 3.87 (s, 4H), 7.14 (s, 4H), 7.30-7.33 (m, 2H), 7.44-7.46 (m, 4H), 7.56-7.66 (m, 6H), 7.75-7.77 (m, 2H), 7.97 (s, 2H); $^{13}$C NMR (CDCl$_3$, Me$_4$Si) δ: 35.5, 125.2, 125.3, 126.4, 127.1, 127.5, 128.3, 128.8 (two peaks were overlapped), 130.7, 130.8 (two peaks were overlapped), 131.0, 133.1, 136.0, 137.7, 139.8.

HRMS (EI) C$_{34}$H$_{24}$: Calculated: 432.1878. Found: 432.1881.

Example 6

Preparation of 6,13-substituted 5,14-dihydropentacene derivative

[Formula 26]

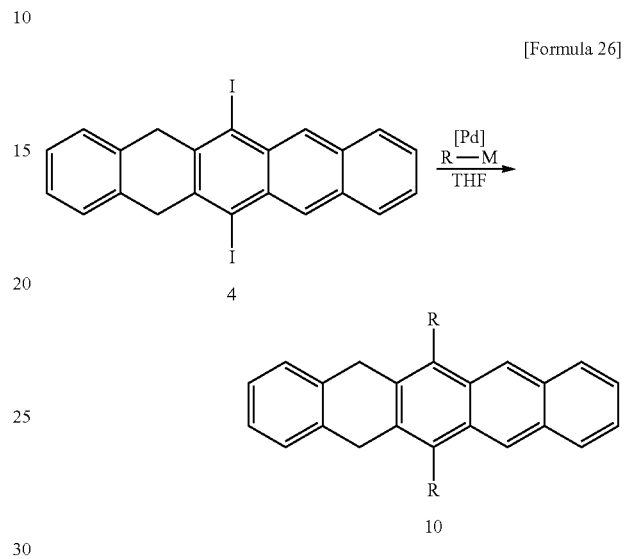

The same procedures as shown in Examples 3 to 5 were repeated except for using the conditions indicated in Table 1 to prepare 6,13-substituted 5,14-dihydropentacene derivatives (compound 10).

TABLE 1

| Example | Reagent R—M | Amount used (eq.) | [Pd] | Reaction conditions | Yield of 10 (%)* |
|---|---|---|---|---|---|
| a | Me$_3$Al | 3.0 | Pd(PPh$_3$)$_4$ | refluxing, 1 d | 86 (82) |
| b | Et$_3$Al | 3.0 | Pd(PPh$_3$)$_4$ | refluxing, 1 d | 84 (75) |
| c | Ph-ZnCl | 3.0 | Pd(PPh$_3$)$_4$ | refluxing, 12 h | 74 (70) |
| d | 2-thienyl-ZnCl | 3.0 | Pd(PPh$_3$)$_4$ | 50° C., 12 h | 94 (72) |
| e | bithienyl-ZnCl | 3.0 | Pd(PPh$_3$)$_4$ | 50° C., 12 h | 86 (70) |
| f | H—≡—TMS | 5.0 | Pd(PPh$_3$)$_4$ | CuI, Et$_3$N, 50° C., 6 h | 92 (84) |
| g | H—≡—TIPS | 5.0 | Pd(PPh$_3$)$_4$ | CuI, Et$_3$N, 50° C., 6 h | 96 (87) |

TABLE 1-continued

| Ex-ample | Reagent R—M | Amount used (eq.) | [Pd] | Reaction conditions | Yield of 10 (%)* |
|---|---|---|---|---|---|
| h |  | 3.0 | Pd(PPh₃)₄ | NaOH, refluxing, 3 d | 80 (73) |

*NMR yield with isolated yield in parentheses

Example 7

Reaction of 6,13-diiodo-5,14-dihydropentacene derivative with palladium complex

[Formula 27]

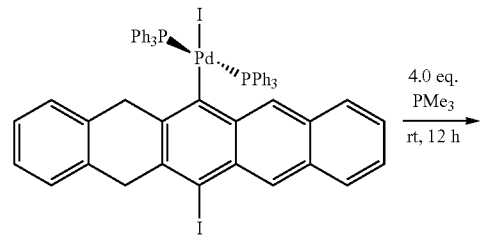

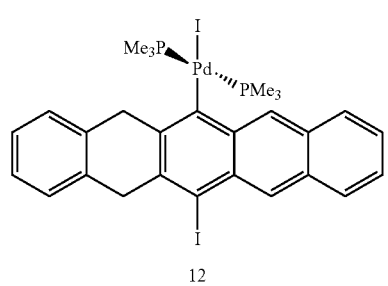

Compound 4 obtained in Example 1 (1 mmol) and Pd(PPh₃)₄ (1.2 mmol) were added to THF (10 ml), and this mixture was reacted at room temperature for 12 hours. The reaction product was diluted with hexane to precipitate a complex, which was then isolated by filtration and dried to give complex compound 11 (NMR yield: 79%, isolated yield: 41%).

Then, to the resulting complex compound 11 (1 mmol), trimethylphosphine (4 mmol) was added and reacted at room temperature for 12 hours. When the reaction product was diluted with hexane and allowed to stand, crystals were precipitated, which were then filtered and dried to give complex compound 12. FIG. 1 shows the results of X-ray structural analysis obtained for complex compound 12.

Example 8

Preparation of 6,13-substituted 5,14-dihydropentacene derivative

[Formula 28]

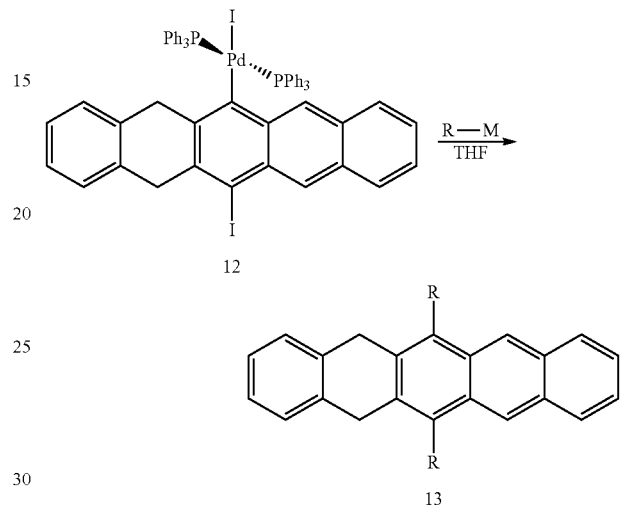

In accordance with the conditions indicated in Table 2, 6,13-substituted 5,14-dihydropentacene derivatives (compound 13) were prepared.

TABLE 2

| Example | Reagent R—M | Amount used (eq.) | Reaction conditions | Yield of 13 (%)* |
|---|---|---|---|---|
| i | Me₃Al | 3.0 | refluxing, 12 h | 99 |
| j | Et₃Al | 3.0 | refluxing, 12 h | 92 |
| k | Ph–ZnCl | 4.0 | refluxing, 12 h | 99 |
| l | 2-thienyl–ZnCl | 4.0 | refluxing, 12 h | 95 |
| m | bithienyl–ZnCl | 4.0 | refluxing, 12 h | 98 |
| n | H—≡—TMS | 5.0 | CuI, Et₃N, refluxing, 12 h | 96 |
| o | H—≡—TIPS | 5.0 | CuI, Et₃N, refluxing, 1 d | 100 |

*NMR yield

As shown above, desired 6,13-substituted 5,14-dihydropentacene derivatives were obtained when the 6,13-diiodo-5,14-dihydropentacene derivative was reacted with a palladium complex and the resulting complex compound was then reacted with organometallic compounds. Since the above complex compound is stably present, it is useful as a reaction intermediate for production of 6,13-substituted 5,14-dihydropentacene derivatives.

INDUSTRIAL APPLICABILITY

The present invention provides a 6,13-dihalogen-5,14-dihydropentacene derivative, which is a novel compound. When using the compound of the present invention, it is possible to produce a 6,13-substituted 5,14-dihydropentacene derivative and further a 6,13-substituted pentacene derivative, etc., in a simpler manner with high selectivity.

The invention claimed is:

1. A 6,13-dihalogen-5,14-dihydropentacene derivative represented by the following formula (I):

[Formula 29]

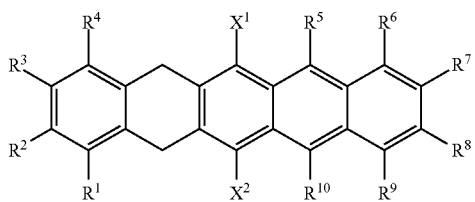

(I)

[wherein $X^1$ and $X^2$, which may be the same or different, are each independently a halogen atom, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group].

2. The derivative according to claim 1, wherein $X^1$ and $X^2$ are each an iodine atom.

3. The derivative according to claim 1, wherein $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ alkyl group; an optionally substituted $C_6$-$C_{20}$ aryl group or an optionally substituted silyl group.

4. The derivative according to claim 1, wherein $R^1$, $R^2$, $R^3$, $R^4$, $R^5$, $R^6$, $R^7$, $R^8$, $R^9$ and $R^{10}$ are each a hydrogen atom.

5. A method for producing a 6,13-substituted 5,14-dihydropentacene derivative represented by the following formula (II):

[Formula 30]

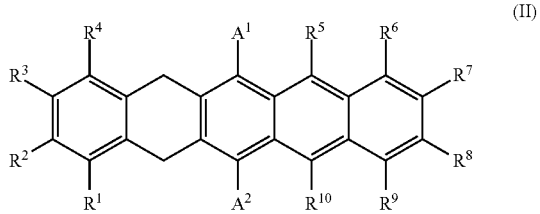

(II)

[wherein $A^1$ and $A^2$, which may be the same or different, are each independently an optionally substituted $C_1$-$C_{20}$ hydrocarbon group; an optionally substituted heteroaryl group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the heteroaryl group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group], said method comprising the step of reacting a 6,13-dihalogen-5,14-dihydropentacene derivative represented by the following formula (I):

[Formula 31]

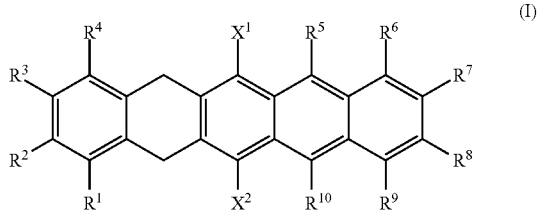

(I)

[wherein $X^1$ and $X^2$, which may be the same or different, are each independently a halogen atom, and $R^1$, $R^2$, $R^3$, $R^4$, $R^5$, $R^6$, $R^7$, $R^8$, $R^9$ and $R^{10}$ are the same as defined in formula (II)] with an organometallic compound comprising $A^1$ or $A^2$ as defined in formula (II) in the presence of a transition metal catalyst.

6. The method according to claim 5, wherein the organometallic compound is selected from the group consisting of an organolithium compound, an organomagnesium compound, an organoaluminum compound, an organozinc compound, an organoboron compound and an organosilyl compound.

7. The method according to claim 5, wherein the organometallic compound is any of compounds represented by formulae (1) to (6):

$$RLi \quad (1)$$

$$RmgY \quad (2)$$

$$R_3Al \quad (3)$$

$$RznY \quad (4)$$

$$RBY_2 \quad (5)$$

$$RSiR'_3 \quad (6)$$

[wherein each R, which may be the same or different, is independently $A^1$ or $A^2$ as defined in formula (II), each Y, which may be the same or different, is independently a halogen atom or a hydroxy group, and R' is a $C_1$-$C_{10}$ alkyl group].

8. The method according to claim 5, wherein the transition metal catalyst comprises a nickel complex or a palladium complex.

9. The method according to claim 5, wherein $A^1$ and $A^2$, which may be the same or different, are each independently an optionally substituted $C_1$-$C_{20}$ alkyl group, an optionally substituted $C_2$-$C_{20}$ alkenyl group, an optionally substituted $C_2$-$C_{20}$ alkynyl group, an optionally substituted $C_6$-$C_{20}$ aryl group or an optionally substituted heteroaryl group.

10. The method according to claim 5, wherein $X^1$ and $X^2$ are each an iodine atom.

11. The method according to claim 5, wherein $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ alkyl group; an optionally substituted $C_6$-$C_{20}$ aryl group or an optionally substituted silyl group.

12. The method according to claim 5, wherein $R^1$, $R^2$, $R^3$, $R^4$, $R^5$, $R^6$, $R^7$, $R^8$, $R^9$ and $R^{10}$ are each a hydrogen atom.

13. A complex compound represented by the following formula (IV):

[Formula 34]

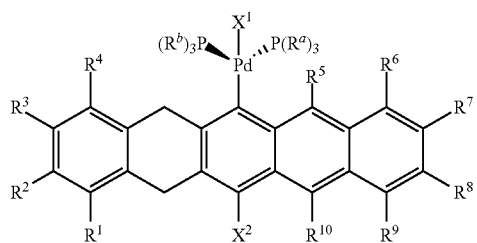

[wherein $X^1$ and $X^2$, which may be the same or different, are each independently a halogen atom, $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group, and $R^a$ and $R^b$, which may be the same or different, are each independently an optionally substituted $C_1$-$C_{20}$ alkyl group or an optionally substituted $C_6$-$C_{20}$ aryl group].

14. A method for producing a 6,13-substituted 5,14-dihydropentacene derivative represented by the following formula (II):

[Formula 35]

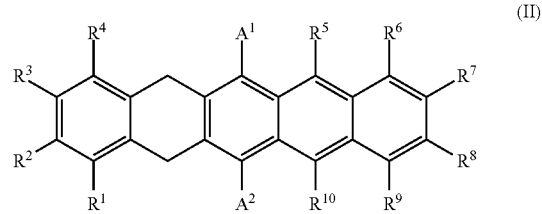

[wherein $A^1$ and $A^2$, which may be the same or different, are each independently an optionally substituted $C_1$-$C_{20}$ hydrocarbon group; an optionally substituted heteroaryl group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the heteroaryl group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group, and $R^1$, $R^2$, $R^3$, $R^4$, $R^5$, $R^6$, $R^7$, $R^8$, $R^9$ and $R^{10}$, which may be the same or different, are each independently a hydrogen atom; an optionally substituted $C_1$-$C_{20}$ hydrocarbon group; an optionally substituted $C_1$-$C_{20}$ alkoxy group; an optionally substituted $C_6$-$C_{20}$ aryloxy group; an optionally substituted $C_1$-$C_{20}$ alkoxycarbonyl group; an optionally substituted $C_6$-$C_{20}$ aryloxycarbonyl group; an optionally substituted carbamoyl group; an optionally substituted amino group or an optionally substituted silyl group, wherein if the hydrocarbon group, the alkoxy group, the aryloxy group, the alkoxycarbonyl group, the aryloxycarbonyl group, the carbamoyl group, the amino group or the silyl group has a substituent(s), the substituent(s) is/are selected from the group consisting of a $C_1$-$C_{10}$ hydrocarbon group, a $C_1$-$C_{10}$ alkoxy group, a $C_6$-$C_{12}$ aryloxy group, an amino group, a hydroxyl group, a halogen atom and a silyl group], said method comprising the step of reacting a complex compound represented by the following formula (IV):

[Formula 36]

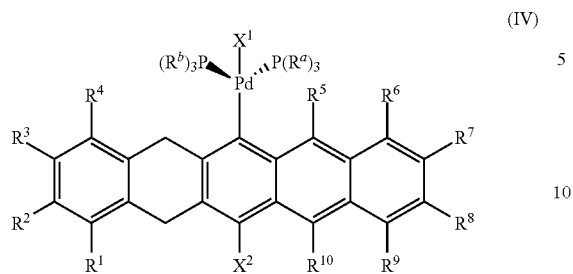

(IV)

[wherein $X^1$ and $X^2$, which may be the same or different, are each independently a halogen atom, $R^1$, $R^2$, $R^3$, $R^4$, $R^5$, $R^6$, $R^7$, $R^8$, $R^9$ and $R^{10}$ are the same as defined in formula (II), and $R^a$ and $R^b$, which may be the same or different, are each independently an optionally substituted $C_1$-$C_{20}$ alkyl group or an optionally substituted $C_6$-$C_{20}$ aryl group] with an organometallic compound comprising $A^1$ or $A^2$ as defined in formula (II).

\* \* \* \* \*